United States Patent [19]
Webb

[11] Patent Number: 5,792,125
[45] Date of Patent: Aug. 11, 1998

[54] COLLECTION TRAY FOR USE IN PELVIC PROCEDURES AND IN PARTICULAR FOR USE IN VAGINAL DELIVERY AND EPISIOTOMY PROCEDURES

[76] Inventor: Nicholas J. Webb, P.O. Box 831, Wrightwood, Calif. 92397

[21] Appl. No.: 762,196

[22] Filed: Dec. 9, 1996

[51] Int. Cl.[6] .................................................. A61M 1/00
[52] U.S. Cl. ........................................... 604/317; 604/319
[58] Field of Search ................................ 604/317, 319, 604/326; 128/849, 852; 4/245.2

[56] References Cited

U.S. PATENT DOCUMENTS

| | | | |
|---|---|---|---|
| 3,386,444 | 6/1968 | Brenner et al. | 128/292 |
| 3,719,188 | 3/1973 | Fisher et al. | 604/317 |
| 4,007,741 | 2/1977 | Waldrop et al. | 128/292 |
| 4,024,590 | 5/1977 | Wendt | 604/317 X |
| 4,076,017 | 2/1978 | Haswell | 128/2 F |
| 4,105,019 | 8/1978 | Haswell | 128/2 F |
| 4,149,537 | 4/1979 | Haswell | 128/292 |
| 4,503,864 | 3/1985 | Powers | 604/317 X |
| 4,553,538 | 11/1985 | Rafelson | 128/852 |
| 4,905,710 | 3/1990 | Jones | 128/852 X |
| 5,170,804 | 12/1992 | Glassman | 128/849 |
| 5,224,679 | 7/1993 | Code | 128/852 X |
| 5,287,860 | 2/1994 | Owens | 128/849 X |
| 5,392,469 | 2/1995 | Adams | 4/245.2 |
| 5,395,394 | 3/1995 | Vancaillie | 128/849 X |
| 5,454,797 | 10/1995 | Haswell | 604/317 |
| 5,487,393 | 1/1996 | Haswell et al. | 604/317 X |

*Primary Examiner*—Sam Rimell
*Attorney, Agent, or Firm*—David P. Gordon; Thomas A. Gallagher; David S. Jacobson

[57] ABSTRACT

A collection tray for use in pelvic procedures includes a single piece molded plastic tray having a planar portion, a basin portion, and a live hinge therebetween. The basin portion is preferably provided with a central drain which is adapted to be coupled to a vacuum line. The basin portion is preferably provided with one or more clip structures for holding an irrigation fluid tube so that irrigation fluid may be easily directed toward the site of the procedure. The tray is preferably manufactured by vacuum forming techniques and the outer edge of the basin portion is preferably rolled down to provide a smooth edge and enhanced structural support. A kit containing the tray includes a fluid collection system and an irrigation system having an articulatable nozzle.

17 Claims, 2 Drawing Sheets

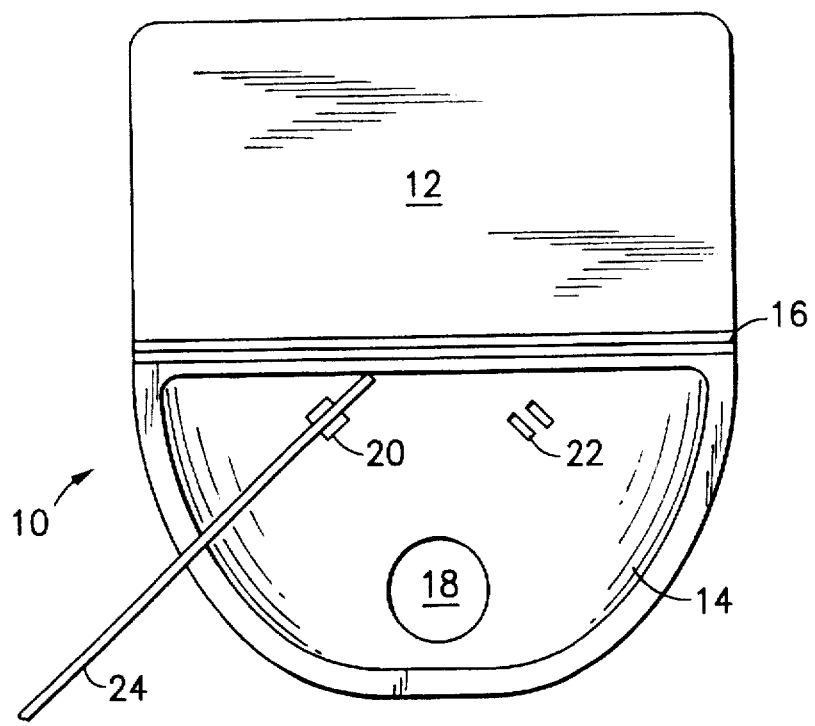
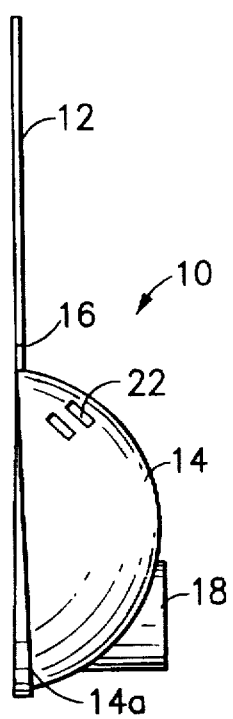
FIG.1  FIG.2
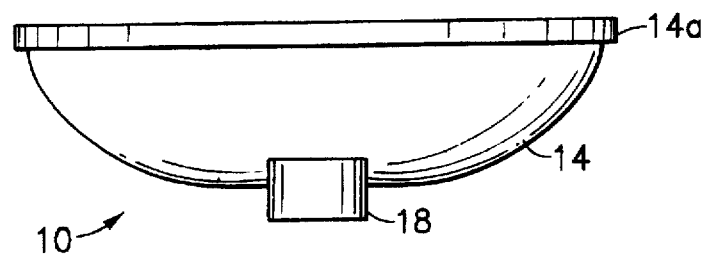
FIG.3
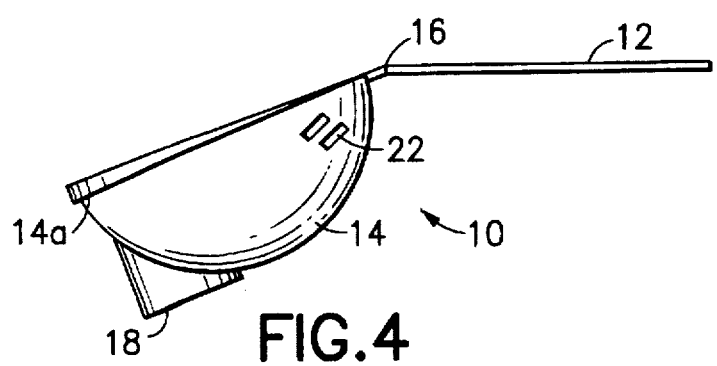
FIG.4

COLLECTION TRAY FOR USE IN PELVIC PROCEDURES AND IN PARTICULAR FOR USE IN VAGINAL DELIVERY AND EPISIOTOMY PROCEDURES

BACKGROUND OF THE INVENTION

1. Field of the Invention

The present invention relates to a device for collecting fluids during pelvic procedures such as obstetric, gynecologic, proctologic or urologic procedures. More particularly, the invention relates to a molded disposable plastic tray having structure for collecting fluids and irrigating a surgical site.

2. State of the Art

During vaginal delivery and other types of pelvic procedures it is necessary to collect and drain fluids (and particles entrained in the fluids) which flow from pelvic tracts. The art discloses several devices for achieving this purpose.

U.S. Pat. No. 3,386,444 to Brenner et al. discloses a surgical drain bag and support for use in urological surgery. The drain bag has four flexible side walls, is shaped like an inverted pyramid, and is provided with a drain in a lower portion. The support includes a number of rods which are attached to the end of an examination table and which suspend the bag in a curtain-like manner. The bag also has a flap which rests against the practitioner's chest and acts as a splash guard. This drain bag is a vast improvement over the previously used drain drawers which impeded physician access to the surgical site. Nevertheless, it is cumbersome to install and relatively expensive to manufacture.

U.S. Pat. No. 4,007,741 to Waldrop et al. discloses a transurethral resection apron system which is similar in concept to the drain bag described above. The apron is somewhat simpler to mount, however. It is provided with four corner ties, two of which are tied to uprights on a urological table, and the other two of which are tied to each other behind the surgeon's neck. While this apron offers some advantages over the drain bag, it is still cumbersome to use and relatively expensive to manufacture. Moreover, the attachment to the surgeon's neck inhibits the surgeon and interferes with the surgical procedure.

U.S. Pat. Nos. 4,076,017, 4,105,019, and 4,149,537 to Haswell disclose various embodiments of a postpartum fluid loss receptacle. The receptacle is formed from a substantially rectangular sheet which is folded along its longitudinal axis such that one edge is folded upon itself and sealed to form a pouch. The open end of the sheet is positioned under the patient's buttocks and is thereby supported. The pouch may hang freely from the examination table, or may be supported in a bucket. While the receptacle is relatively inexpensive to manufacture and relatively easy to use, the pliant sheet material does not readily locate the pocket in a convenient manner. It is easy for the pocket to fill and spill over, or to be mispositioned.

U.S. Pat. No. 5,287,860 to Owens discloses a birthing drape. The drape has the geometry of an inverted top hat, with a distal flap and two proximal stirrups. The distal flap is positioned under the patient's buttocks and the stirrups are attached to the patient's ankles. While the drape has some advantages, it is relatively expensive to manufacture and the ankle support stirrups may result in instability of the drape and discomfort for the patient.

U.S. Pat. No. 5,454,797 to Haswell discloses a combined pelvic tray, work station, and fluid collection device. The tray is a rigid sheet of plastic or stainless steel having a first portion which is positioned under the patient's buttocks and a second portion which has a fluid receiving well, receptacles for solutions, instruments, and swabs. A raised fluid dam or dike separates the first and second portions and prevents fluids from flowing under the patient's buttocks. While the rigid plastic tray is easy to use and relatively inexpensive to manufacture, the dam is not completely effective, and the location of the proximal portion of the tray can obscure the surgical site. More specifically, the dam may simply direct the flow of fluids off the side of the tray onto the floor; and the location of the proximal portion of the tray prevents access to the surgical site from below the horizontal plane. In addition, the fluid receiving well is relatively small and is likely to fill quickly.

During vaginal deliveries, it is common to perform an episiotomy. This procedure releases relatively large quantities of blood which must be collected. The above-described devices are more or less successful in collecting blood during an episiotomy procedure. In addition to the need to collect blood during the episiotomy procedure, the flow of blood obscures the surgical site and it is necessary to irrigate the surgical site. The prior art of fluid collection devices does not address this need for irrigation during episiotomy procedures.

SUMMARY OF THE INVENTION

It is therefore an object of the invention to provide a collection tray for use in pelvic procedures which is easy to use and inexpensive to manufacture.

It is also an object of the invention to provide a collection tray for use in pelvic procedures which has a large collection region and a drain.

It is also a particular object of the invention to provide a collection tray which minimizes the risk of blood born or fluid born pathogens from contaminating health care workers.

It is another object of the invention to provide a collection tray for use in pelvic procedures which does not obscure the surgical site.

It is still another object of the invention to provide a collection tray for use in pelvic procedures which accommodates an irrigation tube for flushing the surgical site.

It is also an object of the invention to provide a collection tray with a controllable irrigation system.

It is another object of the invention to provide an apparatus for irrigating an episiotomy site while concurrently collecting vaginal fluids.

In accord with these objects which will be discussed in detail below, the collection tray of the present invention includes a single piece plastic tray having a planar first portion, a bowl-like second portion, and a live hinge therebetween. The bowl portion is preferably provided with a central drain which is adapted to be coupled to a vacuum line or to be coupled to a collection tube and vessel which can be pre-connected to the drain during manufacture to facilitate rapid deployment of the collection tray. The bowl portion is also preferably provided with one or more clip structures for holding an irrigation fluid tube so that irrigation fluid may be easily directed toward the site of the procedure. A presently preferred irrigation fluid tube for use with the invention includes a spike for connection to a sterile water bottle, an inline valve for controlling the flow of water, and an articulate nozzle for directing the flow of water to the surgical site.

Preferred aspects of the invention include manufacturing the tray by vacuum forming techniques, and die cutting the

3 outer edge of the bowl portion to provide a smooth edge. The presently preferred material for manufacturing the tray is a medical grade gamma stable low density polyethylene such as PETG.

Additional objects and advantages of the invention will become apparent to those skilled in the art upon reference to the detailed description taken in conjunction with the provided figures.

BRIEF DESCRIPTION OF THE DRAWINGS

FIG. 1 is a top plan view of a presently preferred embodiment of the collection tray of the invention shown with an irrigation tube;

FIG. 2 is a side elevation view of the collection tray of FIG. 1;

FIG. 3 is a proximal end elevation view of the tray of FIG. 1;

FIG. 4 is a view similar to FIG. 2 showing the tray folded to a presently preferred configuration for use.

DETAILED DESCRIPTION OF THE PREFERRED EMBODIMENTS

Figure 5:
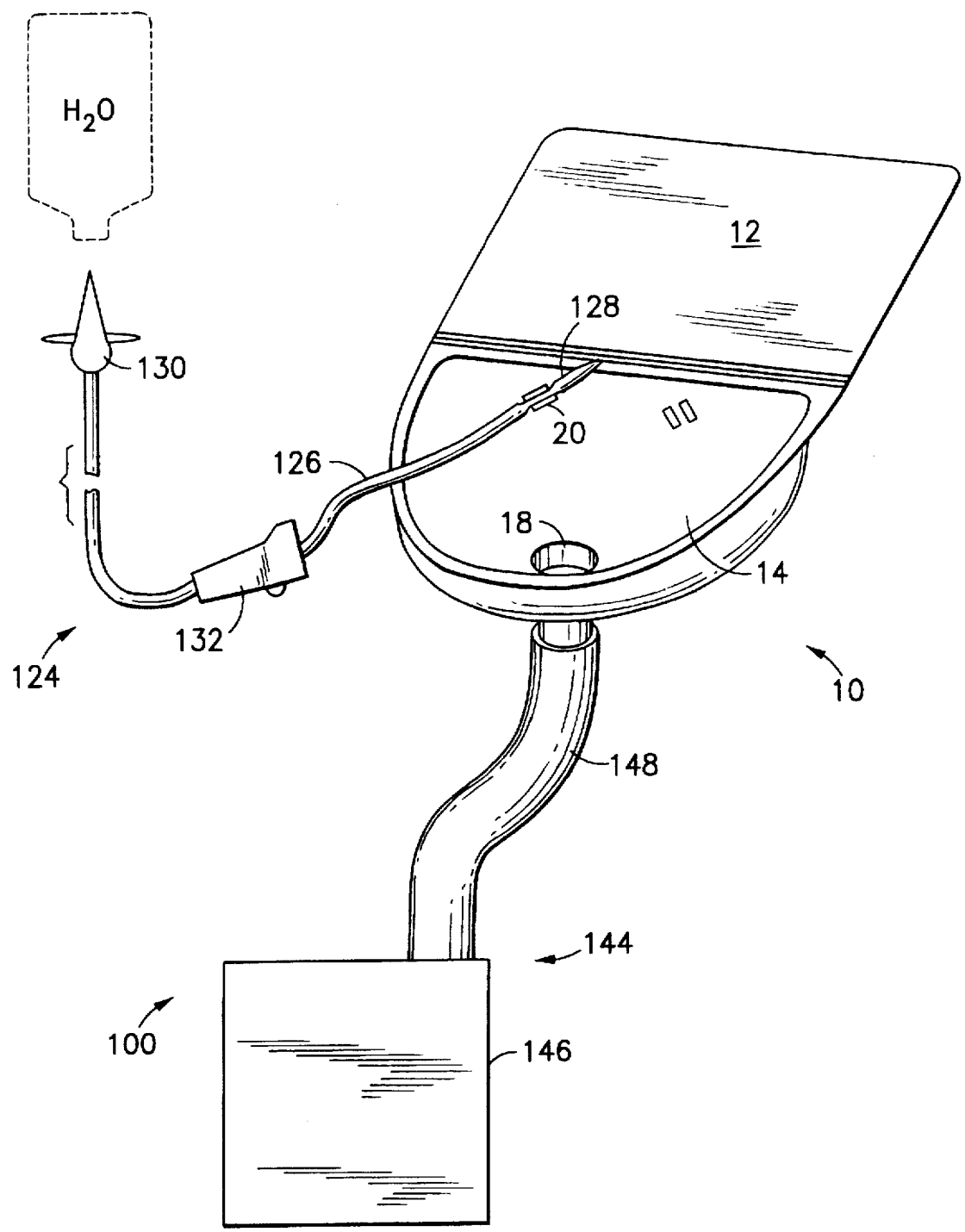
FIG. 5 is a perspective view of a collection tray kit according to the invention having an attached collection vessel and an irrigation system with an articulatable nozzle.

Referring now to FIGS. 1 through 3, a collection tray 10 according to the invention is a one-piece molded plastic member having a planar portion 12, a bowl-like or basin portion 14, and a live hinge 16 therebetween. The bowl portion 14 is preferably provided with a central drain 18 which is adapted with a luer, screw, or other structure to be coupled to a vacuum line (not shown) or to a fluid collection vessel as described below with reference to FIG. 5. The bowl portion is also preferably provided with one or more clip structures 20, 22 for holding an irrigation fluid tube 24 so that irrigation fluid may be easily directed toward the site of the procedure. Those skilled in the art will appreciate that the clip structures 20, 22 may be easily formed in a single molding process by providing a pair of spaced apart raised portions between which a tube may be held as shown in FIG. 1.

According to the presently preferred embodiment, the outer edge 14a of the bowl or basin portion 14 is rolled down as shown in FIGS. 2 and 3. This provides a smooth periphery and adds structural support to the basin portion 14.

In use, the tray 10 is placed so that the planar portion is positioned under the patient's buttocks. If desired, the planar portion can be affixed to the operating table with adhesive tape. Prior to placement, however, it is preferred that the tray be folded at the live hinge 16 so that the basin portion 14 is angled down from the planar portion 12 as shown in FIG. 4. This provides a clear angle of view of the procedural site, enhances the position of the clips 20, 22, and lowers the drain 18 so that collected fluids are readily drained from the basin 14. As shown in FIG. 4, the basin portion is folded (bent) approximately 20° C. relative to the planar portion. Bending a greater or lesser amount may be preferable for different procedures. It will be understood, however, that the live hinge portion of the tray should be constructed so that the basin portion can be bent and maintained over a large range relative to the planar portion (e.g., 0–60 degrees) and so that once bent, will maintain itself in a relatively stable angular position relative to the planar portion.

Those skilled in the art will appreciate that the tray 10 may be made to have different dimensions for different purposes. Small trays may be used for smaller patients and large trays may be used for larger patients. According to the presently preferred embodiment, a general purpose tray 10 is approximately fourteen inches from side to side and approximately sixteen inches from the proximal edge of the basin 14 to the distal edge of the planar portion 12. The deepest part of the basin 14 is approximately three and one half inches; and the rolled portion 14a is approximately 0.375 inches deep. It will be appreciated that the collection tray 10 provides a relatively large collection basin 14 which is easily positioned and easily drained. The tray 10 is easy to manufacture, easy to use, and does not interfere with the procedure. It will also be appreciated that sterile trays, packed in plastic bags can be stacked one inside another for economical shipment and storage. The inexpensive plastic trays are disposable and/or recyclable. The presently preferred material for manufacturing the tray is a medical grade gamma stable low density polyethylene such as PETG.

As mentioned above, the tray is intended to be connected to a fluid collection conduit and is preferably also used with an irrigation conduit. FIG. 5 shows an exemplary arrangement of a kit according to the invention which includes a tray, an irrigation system, and a fluid collection vessel. Turning now to FIG. 5, a kit 100 according to the invention includes a tray 10 as described above together with an irrigation system 124 and a fluid collection system 144. The irrigation system 124 includes a medical grade tube 126 having an articulatable nozzle 128 at one end and a connection spike 130 at the other end. A clip or roller valve 132 is arranged on the tube at a convenient location. The articulatable nozzle 128 is preferably constructed of an inexpensive malleable plastic material and the spike 130 is preferably adapted to make a fluid connection to a standard sterile water bottle. The fluid collection system 144 preferably includes a plastic container 146 and a flexible drain conduit 148 which couples the central drain 18 of the tray 10 to the container 146.

The kit 100 shown in FIG. 5 may be pre-assembled during manufacturing and packaged together in a single shipping bag for rapid deployment. Disposal of the kit may be accomplished by placing the irrigation system 124 into the basin 14 and closing the planar portion 12 of the tray 10 over the basin and securing it with adhesive tape. Pre-cut pieces of adhesive tape may also be packaged with the kit. The used kit may then be placed back in its original shipping bag for environmentally safe disposal.

There have been described and illustrated herein a preferred embodiment of a collection tray for use in pelvic procedures. While a single preferred embodiment of the invention has been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while particular geometric shapes have been shown, it will be recognized that other similar shapes could be used with similar results obtained. Moreover, while particular configurations have been disclosed in reference to the tube clips, it will be appreciated that other configurations could be used as well. Furthermore, while the basin has been disclosed as having a drain, it will be understood that given the relatively large size of the basin, a drain may be unnecessary for some procedures. Further yet, while a live hinge has been disclosed and is preferred, it will be appreciated that other types of hinges could be utilized. It will therefore be appreciated by those skilled in the art that yet other modifications could be made to the provided invention without deviating from its spirit and scope as so claimed.

I claim:

1. A collection try for use in pelvic procedures, comprising:

a single piece molded plastic tray having a planar portion, a bowl-shaped basin portion having a lower surface defining a drain, and a live hinge therebetween.

2. A collection tray according to claim 1, wherein:

said bowl-shaped basin portion is concave and substantially round.

3. A collection tray according to claim 1, wherein:

said drain is adapted to be coupled to a vacuum line.

4. A collection tray according to claim 1, wherein:

said bowl-shaped basin portion includes a tube holding structure.

5. A collection tray according to claim 1, wherein:

said tube holding structure comprises a clip integral with said bowl-shaped basin portion.

6. A collection tray according to claim 1, wherein:

said bowl-shaped basin portion has a rolled edge.

7. A collection tray for use in pelvic procedures, comprising:

a) a planar support means for location beneath a patient's buttocks;

b) a bowl-shaped basin having a lower surface defining a drain coupled to said support means; and c) foldable means for coupling said basin to said support means and for angularly positioning said basin relative to said support means.

8. A collection tray according to claim 7, wherein:

said foldable means is a live hinge.

9. A collection tray according to claim 7, wherein:

said basin is concave and substantially round, and said drain is a central drain.

10. A collection tray according to claim 9, wherein:

said drain is adapted to be coupled to a vacuum line.

11. A collection tray according to claim 7, further comprising:

d) a tube holding structure coupled to said basin.

12. A collection tray according to claim 7, wherein:

said tube holding structure comprises a clip.

13. A kit for use in pelvic procedures, comprising:

a) a single piece molded plastic tray having a planar portion and a bowl-like portion with a live hinge therebetween, and a drain in said bowl-like portion, said bowl-like portion also including a tube holding structure;

b) an irrigation system including a tube having an articulate nozzle at one end and a fluid connection means at another end for connecting said tube to a source of irrigant, with a valve means between the ends of said tube for controlling the flow of irrigant, wherein one of said tube and said nozzle is adapted to be held by said tube holding structure;

c) a fluid collection container; and d) a fluid conduit coupled to said fluid collection container and said drain.

14. A kit according to claim 13, wherein:

said nozzle is made of malleable plastic.

15. A kit according to claim 13, wherein:

said fluid connection means is a spike.

16. A kit according to claim 13, wherein:

said valve means is a roller valve.

17. A kit according to claim 13, wherein:

said valve means is a pinch valve.

\* \* \* \* \*